United States Patent
Krause et al.

(10) Patent No.: US 7,443,518 B2
(45) Date of Patent: Oct. 28, 2008

(54) MEASURING INSTRUMENT, IN PARTICULAR FOR TRANSMISSION MEASUREMENT IN VACUUM SYSTEM

(75) Inventors: Jochen Krause, Dresden (DE); Holger Proehl, Dresden (DE)

(73) Assignee: Von Ardenne Anlagentechnik GmbH, Dresden (DE)

( * ) Notice: Subject to any disclaimer, the term of this patent is extended or adjusted under 35 U.S.C. 154(b) by 2 days.

(21) Appl. No.: 11/400,857

(22) Filed: Apr. 10, 2006

(65) Prior Publication Data
US 2006/0256351 A1 Nov. 16, 2006

(30) Foreign Application Priority Data

| Apr. 20, 2005 | (DE) | ......................... 10 2005 018 530 |
| May 31, 2005 | (DE) | ......................... 10 2005 025 385 |

(51) Int. Cl.
G01B 11/06 (2006.01)
G01B 9/02 (2006.01)
G01D 5/36 (2006.01)

(52) U.S. Cl. ....................... 356/632; 356/488; 356/494; 356/499; 250/231.14; 250/237 G

(58) Field of Classification Search ................. 356/601, 356/625–632, 499, 494, 488; 250/339.06, 250/237 G, 231.14, 339.08
See application file for complete search history.

(56) References Cited

U.S. PATENT DOCUMENTS

| 3,775,012 | A | * | 11/1973 | Ling et al. ................... 356/625 |
| 4,243,882 | A | * | 1/1981 | Yasujima et al. ........ 250/339.06 |
| 4,629,886 | A | * | 12/1986 | Akiyama et al. ......... 250/237 G |
| 4,632,548 | A | * | 12/1986 | Gunter et al. ............... 356/28.5 |
| 4,676,645 | A | * | 6/1987 | Taniguchi et al. ........... 356/494 |
| 4,970,388 | A | * | 11/1990 | Nishimura et al. ......... 250/237 G |
| 4,975,571 | A | * | 12/1990 | McMurtry et al. ....... 250/231.16 |
| 4,979,826 | A | * | 12/1990 | Ishizuka et al. ............. 356/499 |
| 5,015,096 | A | * | 5/1991 | Kowalski et al. ............ 356/613 |
| 5,035,507 | A | * | 7/1991 | Nishioki et al. ............. 356/499 |
| 5,066,130 | A | * | 11/1991 | Tsukiji et al. ............... 356/494 |
| 5,120,132 | A | * | 6/1992 | Spies et al. ................. 356/499 |

(Continued)

FOREIGN PATENT DOCUMENTS

DE    28 24 583 C4    12/1979

(Continued)

*Primary Examiner*—Sang Nguyen
(74) *Attorney, Agent, or Firm*—Heslin Rothenberg Farley & Mesiti P.C.; Victor A. Cardona, Esq.

(57) ABSTRACT

A measuring instrument, in particular for transmission measurement with transparent substrates, comprises a measuring head with a light emitting element for emitting a light beam and a light receiver element for recording an incident light beam, and a retro-reflector for reflection of the emitted light beam. The measuring instrument allows transmission measurements to be carried out on transparent substrates with only one reflection measuring head. The measuring instrument also allows reflection measurements to be carried out, for example on non-transparent substrates or by tilting the measuring head and covering the retro-reflector. The measuring instrument only requires one measuring head and can therefore be produced more cost-effectively. It does not require calibration, as the retro-reflector also reflects the light in the original direction in the case of oblique incidence and in the event of positional changes caused by process or operational factors (vibrations etc.).

6 Claims, 2 Drawing Sheets

U.S. PATENT DOCUMENTS

Figure 1:
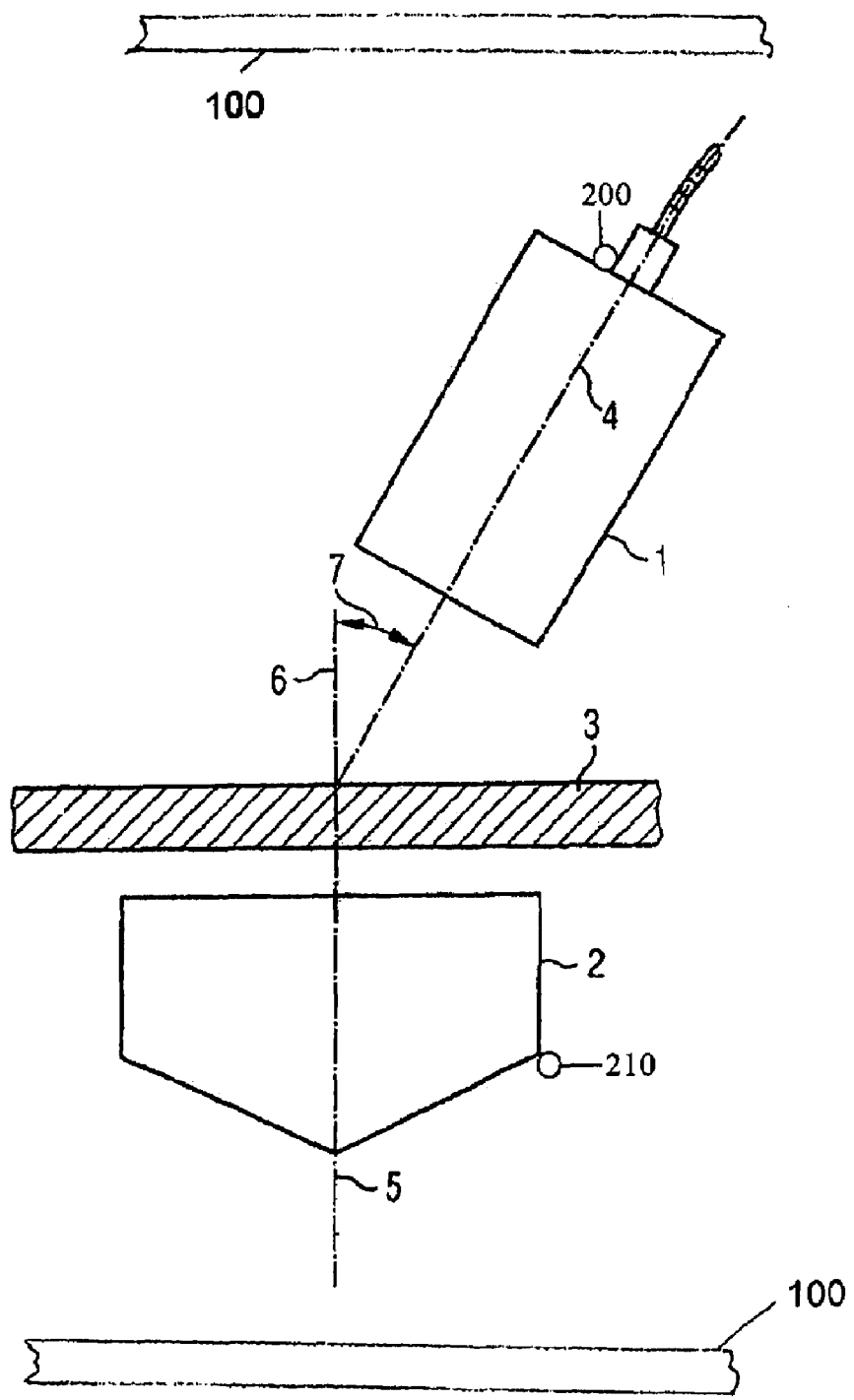

| | | | | |
|---|---|---|---|---|
| 5,187,545 A | * | 2/1993 | Allgauer | 356/482 |
| 5,220,463 A | * | 6/1993 | Edelstein et al. | 359/857 |
| 5,404,220 A | * | 4/1995 | Takeuchi et al. | 356/488 |
| 5,491,551 A | * | 2/1996 | Mattson | 356/451 |
| 5,541,729 A | * | 7/1996 | Takeuchi et al. | 356/488 |
| 5,991,040 A | * | 11/1999 | Doemens et al. | 356/614 |
| 6,392,807 B1 | * | 5/2002 | Barbarossa et al. | 359/578 |
| 6,577,401 B1 | * | 6/2003 | Matsumoto | 356/499 |
| 6,791,698 B2 | * | 9/2004 | Doemens et al. | 356/614 |

FOREIGN PATENT DOCUMENTS

| | | |
|---|---|---|
| DE | 44 18 180 A1 | 1/1996 |
| DE | 195 06 312 C2 | 8/1996 |

* cited by examiner

MEASURING INSTRUMENT, IN PARTICULAR FOR TRANSMISSION MEASUREMENT IN VACUUM SYSTEM

BACKGROUND OF THE INVENTION

The invention concerns a measuring instrument, in particular for transmission measurement in transparent substances.

For in-situ process monitoring in vacuum systems for coating substrates, in particular for coating thickness measurement for substrates, measurements are carried out which are based on recording the extinction, i. e. the reduction in the light of a light beam shone on the substrate caused by absorption in the reflection or transmission of the light.

Two different approaches are taken for such measurements.

In the case of a measurement based on extinction caused by transmission, measuring heads are located on both sides of the transparent substrate, whereby one measuring head comprises an emitter unit for emitting light and the other measuring head comprises a receiver unit for receiving the component of the emitted light passing through the substrate. Both measuring heads are usually aligned towards each other in such way that the emitted light beam impinges on the substrate vertically and reaches the second measuring head after passing through the substrate.

The drawback to this solution is the relatively expensive and complex equipment required as a result of using two measuring heads as well as the risk of measuring errors on account of an undesired coating on at least one of the two measuring heads. Moreover, the calibration of the instrumentation is complicated and sensitive.

In the case of a measurement based on extinction caused by reflection, one measuring head is located on one side of the substrate (this must always be the coated side in the case of non-transparent substrates). This measuring head comprises an emitter unit for emitting light and a receiver unit for receiving the component of the emitted light reflected from the substrate. The measuring head is aligned towards the substrate in such a way that the reflected light beam returns to the measuring head.

The drawback of the solution is that transmission measurements cannot be carried out and hence the absorbent effect of the substrate itself cannot be ascertained. The calibration of this instrumentation is also complicated and sensitive.

BRIEF SUMMARY OF THE INVENTION

The task of the present invention therefore involves providing a measuring device, in particular for transmission measurement with transparent substrates, which exhibits low space requirements with a simple and cost-effective instrumentation setup, which is easily accessible for cleaning and maintenance purposes and which is tolerant in respect to calibration errors.

In the sense of the present invention, the task was solved by a transmission instrument with the features of claim 1. Advantageous embodiments of the invention are the object of the dependent claims.

The measuring instrument corresponding to the invention, in particular for transmission measurement for transparent substrates, comprises a measuring head with a light transmission element for emitting a beam of light and a light receiver unit for recording an incident beam of light and is characterized such that a retro-reflector is also provided for reflection of the emitted beam of light.

The term retro-reflector refers to a so-called triple mirror in the sense of the present patent or a similarly understood arrangement of several triple mirrors. Such triple mirrors exhibit three mirrored areas which are aligned to towards each other in such a way that each mirrored area forms a right angle with each of the two other mirrored areas. Triple mirrors have the property of reflecting light with minor lateral misalignment in the same direction from which it arrives. This principle typically forms the basis of reflectors known as "cats eyes".

The measuring instrument corresponding to the invention allows transmission measurements to be carried out with transparent substrates with only one measuring head, or more precisely a reflection measuring head which can both emit light and record incident light. At the same time, the measuring instrument also allows reflection measurements to be carried out, for example on non-transparent substrates or by covering the reflector.

The measuring instrument only requires one measuring head and can therefore be produced more cost-effectively than conventional measuring instruments for transmission measurements. It also does not require calibration, as the retro-reflector also reflects the light in cases of oblique incidence of light into the original device.

In an embodiment of the invention, the retro-reflector is designed as a cube corner prism.

The arrangement of the three mirrored areas in a cube corner prism corresponds to the aforementioned arrangement, i.e. each mirrored area is vertical to each of the other two mirrored areas as in the die surfaces coinciding in the corner point of a die. The advantage of prisms, in particular those made from optical glass, is the low energy losses and the straightforward cleaning.

The measuring head is advantageously positioned at an angle to the main axis of the retro-reflector other than zero.

In particular when carrying out transmission measurements, it is advantageous to prevent the light beam from vertical incidence on the substrate, in order to avoid incorrect measurements on account of light components which are reflected from the substrate. If the measuring head is positioned at an angle to the main axis of the retro-reflector other than zero, so that the light beam is also incident on the substrate at an angle to the normal axis of the substrate other than zero, the light receiver unit only records the component of emitted light passing through the substrate which reaches the retro-reflector and which returns to the measuring head after passing through the substrate again. Light components reflected from the substrate, however, are deflected away from the measuring head and hence do not affect the measurement.

The measuring instrument corresponding to the invention is preferably located in a vacuum system for coating flat substrates in such a way that the measuring bead is positioned on the one side of the substrate plane and the retro-reflector is located on the other side of the substrate plane.

This arrangement enables use of the measuring instrument in those systems both for transmission measurements and for reflection measurements. Vacuum systems which exhibit the measuring instrument corresponding to the invention enable highly accurate in-situ measurements of coating thicknesses, light transparency or absorption of the coated substrates etc.

The light emitted from the light emitter unit is advantageously projected onto the substrate at an angle to the normal axis of the substrate plane other than zero if the measuring instrument is in operation.

As already explained above, it can be advantageous to not allow the light beam to be incident vertically on the substrate in order to avoid incorrect measurements on account of light components which are reflected from the substrate. However, for space-saving reasons it may be necessary to arrange the retro-reflector in a manner different from this.

It is also therefore an advantage to arrange the reflector in such a way that the main axis of the retro-reflector essentially runs parallel to the normal axis of the substrate plane.

The measuring head and/or the retro-reflector are preferably mounted so as to swivel in respect to the substrate plane.

In this way the measuring instrument is lightweight and rapidly adjustable to different measuring modes such as transmission measurement and reflection measurement.

For transmission measurement, the measuring head is preferably positioned at an angle to the substrate surface other than zero, in order to prevent the measurement from being falsified by reflected light.

A second measuring head can be provided for the simultaneous measurement of transmission and refection. Both measuring heads must be aligned at an angle to the substrate surface other than zero such that the reflected component of the light emitted from the first measuring head can be received by the second measuring head.

Alternatively, a second retro-reflector 105 and a cover 106 can be provided instead of the second measuring head, which in turn reflects the light reflected from the substrate surface, with the result that it returns to the first measuring head. If both retro-reflectors can be designed so as to be coverable, a reflection measurement can optionally be carried out by covering the first reflector, while a transmission measurement can be carried out by covering the second reflector, without having to calibrate components of the instrumentation.

If only one measuring head and one reflector head are provided, a transmission measurement can be carried out by deflecting the measuring head at an angle other than zero onto the retro-reflector located below the substrate, and a reflection measurement can be carried out by aligning the measuring head vertically to the substrate surface and, if necessary, swiveling the retro-reflector out of the light beam or covering it.

If the retro-reflector is covered when aligning the measuring head vertically to the surface, the signal measured only contains the reflected components. If, on the other hand, the retro-reflector is not covered when aligning the measuring head vertically to the surface, the signal measured contains the reflected and transmitted components. The transmitted component can easily be ascertained from these two signals through calculation.

BRIEF DESCRIPTION OF THE DRAWING FIGURE

The invention will now be explained in more detail on the basis of an embodiment example and an accompanying drawing. At the same time, FIG. 1 provides a diagram for the structure of the transmission measuring instrument.

Figure 2:
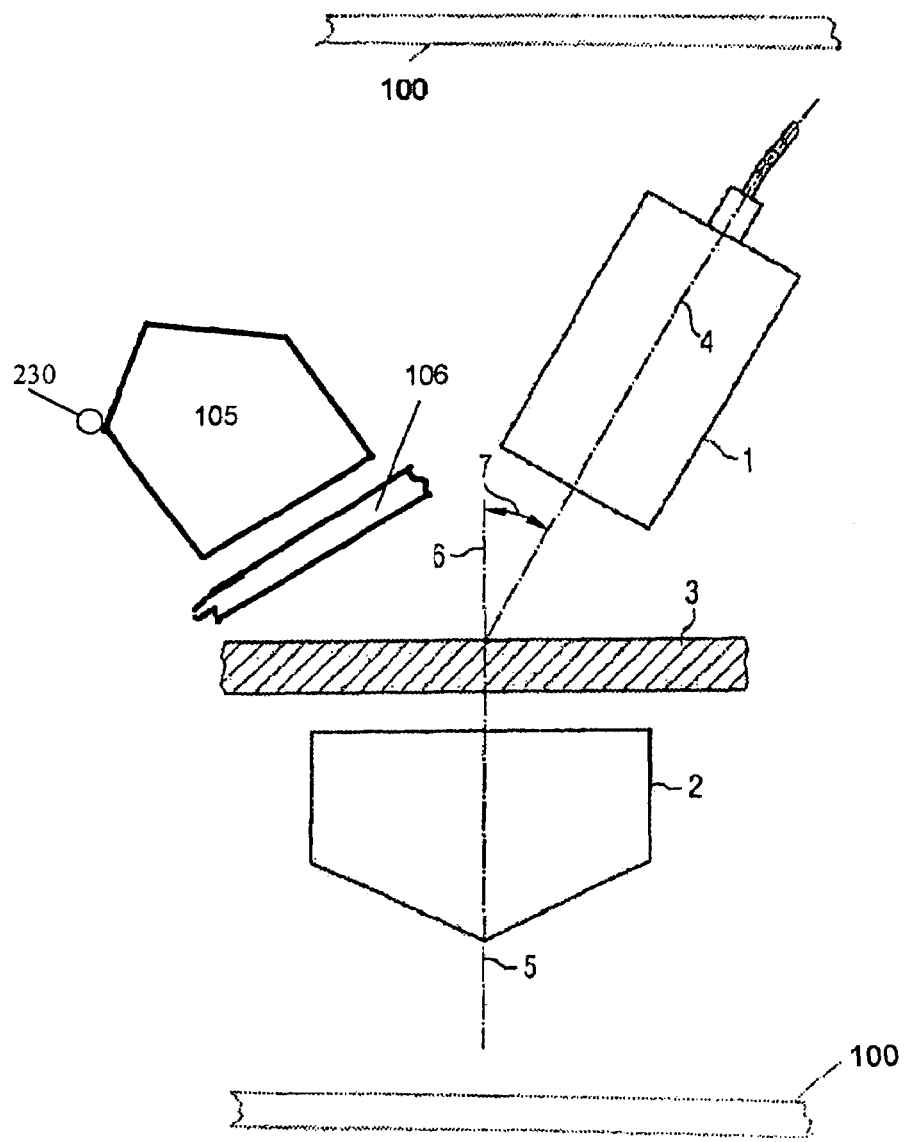

FIG. 2 is a block diagram of another embodiment of a transmission measuring instrument in accordance with the present invention.

DETAILED DESCRIPTION

In a vacuum system 100 for coating two-dimensional measuring substrates, a measuring head 1 with a light emitting element for emitting a beam of light and a light receiver element for recording an incident beam of light as well as a retro-reflector 2 are arranged in such a way that the measuring head 1 is located on the one side of the substrate plane 3 and the retro-reflector 2 is located on the other side of the substrate plane 3.

The retro-reflector 2 is realized as a cube corner prism made from optical glass in the embodiment example.

The light emission direction 4 of the light emitted from the light emitting element of the measuring head 1 comprises an angle 7 other than zero with the normal axis 6 of the substrate plane 3, with the result that the light is projected onto the substrate 3 at this angle 7, if the measuring instrument is in operation.

The retro-reflector 2 is positioned in such a way that its main axis 5 comprises an angle 7 other than zero with the light emission direction 4 of the light emitted by the light emitting element of the measuring head 1.

The main axis 5 of the retro-reflector 2 runs vertically to the substrate plane 2 and therefore coincides with the normal axis 6 of the substrate plane 3.

The measuring head 1 and retro-reflector 2 are mounted so as to swivel (e.g., on a first swivel 200 and a second swivel 210, respectively) in respect to the substrate plane. Second retro-reflector 105 is mounted so as to swivel on a third swivel 230.

What is claimed is:

1. A vacuum coating installation comprising a measuring instrument for reflection and transmission measurements with transparent substrates, comprising:

a measuring head with a light emitting element for emitting a light beam and a light receiver element for recording an incident light beam, arranged on a first side of the substrate plane;

a retro-reflector for reflection of the emitted light beam, arranged on a second side of the substrate plane;

means for preventing the light beam from impinging on the retro-reflector ; and a second retro-reflector, arranged on a first side of the substrate plane, and means for preventing the light beam from impinging on the second retro-reflector.

2. The vacuum coating installation according to claim 1, wherein the means for preventing the light beam from impinging on the retro-reflector comprises a swivelling mounting of the measuring head.

3. The vacuum coating installation according to claim 1, wherein the means for preventing the light beam from impinging on the retro-reflector comprises a swivelling mounting of the retro-reflector.

4. The vacuum coating installation according to claim 1, wherein the means for preventing the light beam from impinging on the retro-reflector comprises a cover for selectively covering or uncovering the retro-reflector.

5. The vacuum coating installation according to claim 1, wherein the means for preventing the light beam from impinging on the second retro-reflector comprises a swivelling mounting of the second retro-reflector.

6. The vacuum coating installation according to claim 1, wherein the means for preventing the light beam from impinging on the second retro-reflector comprises a cover for selectively covering or uncovering the second retro-reflector.

* * * * *